United States Patent [19]
Caillouette

[11] Patent Number: 5,425,377
[45] Date of Patent: Jun. 20, 1995

[54] PH MEASUREMENT OF BODY FLUID

[76] Inventor: James C. Caillouette, 685 Oak Knoll Cir., Pasadena, Calif. 91106

[21] Appl. No.: 295,399
[22] Filed: Aug. 25, 1994
[51] Int. Cl.⁶ .......................................... A61B 10/00
[52] U.S. Cl. .................................. 128/759; 604/1
[58] Field of Search ............... 128/749, 759; 604/1; 33/755, 758–760, 511, 512

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 4,820,259 | 4/1989 | Stevens ............................ 604/1 |
| 4,862,899 | 9/1989 | Bucaro ........................... 128/759 |
| 5,063,930 | 11/1991 | Nucci ............................ 128/632 |
| 5,147,288 | 9/1992 | Schiavo ........................... 604/1 |

Primary Examiner—Max Hindenburg
Attorney, Agent, or Firm—William W. Haefliger

[57] ABSTRACT

The method of measuring pH of vaginal moisture, which includes providing a pH indication, color comparison measurement, and swabbing structure on a carrier stick; manipulating the stick between its opposite ends, to obtain pH indication of vaginal moisture at one end of the stick; visually interpreting that indication to also obtain pH measurement of such moisture near that one end of the stick; again manipulating the stick between its opposite ends, including endwise reversing it, to swab the vaginal cavity in the area from which pH indication was obtained; and disposing of the stick, whereby disposition of the pH indication, measurement and swabbing structure is thereby obtained in one disposal step.

20 Claims, 1 Drawing Sheet

PH MEASUREMENT OF BODY FLUID

BACKGROUND OF THE INVENTION

This invention relates generally to pH measurement of body fluid, such as vaginal fluid, and more particularly, to a rapid, easily performed method of obtaining such measurement as well as subsequently absorbing excess fluid at the measurement site.

There is continual need to obtain pH measurement of vaginal fluid, as for example in the determination of whether amniotic fluid has escaped into the vagina, during late pregnancy. Amniotic fluid is normally alkaline, whereas vaginal moisture is normally acidic. This difference enables testing for pH, using a test strip, such as a Nytrazine strip, typically handled by forceps when inserted into the vagina, for pH test purposes; however, the procedure and subsequent procedures to determine acidity or alkalinity requires considerable manipulation, including cutting of a test strip, grasping of the cut strip by forceps manipulation, subsequent insertion with risk of separation of the strip from the forceps, recovery of the strip, and its examination.

There is need for a simple, rapidly carried out method which obviates problems associated with the conventional procedure; also, there is need for ease of excess moisture removal from the vagina, at the time of the pH test.

SUMMARY OF THE INVENTION

It is a major object of the invention to provide a significantly improved method which meets the above need, and overcomes prior problems, as referred to. Basically, the method of the invention includes the steps:
 a) providing a pH indication, color comparison measurement, and swabbing means on a carrier stick,
 b) manipulating the stick between its opposite ends to obtain pH indication of vaginal moisture at one end of the stick,
 c) visually interpreting that indication to also obtain pH measurement of such moisture near that one end of the stick,
 d) again manipulating the stick between its opposite ends, including endwise reversing it, to swab the vaginal cavity in the area from which pH indication was obtained,
 e) and disposing of the stick, whereby disposition of the pH indication, measurement and swabbing means is thereby obtained in one disposal step.

As will appear, the a) step may include adhering a pH indication strip to one end of the stick and adhering a pH measurement colorimeter strip to the stick adjacent the pH indication strip, but between the indication strip and the swabbing means, leaving stick extent free for manual manipulation.

It is another object to provide pH measurement means having color gradations in a series sequence, including locating the series lengthwise along the stick, adjacent the indication means. As will be seen, pH measurement means may be provided by winding it about one end of the stick.

A further object includes maintaining an elongated gap along the stick between the pH measurement means and the swabbing means, whereby the stick may be grasped at the gap for manipulation. In this regard, the swabbing means may be provided by attaching a moisture-absorbing swab to the other end of the stick, and in lengthwise spaced relation to both pH indicating means and pH measurement means.

Yet another object includes the provision of the pH measurement means to have a pH numerical sequence in a series associated with the color gradations, and including also locating the numerical sequence lengthwise along the stick.

Apparatus incorporating the invention includes, in combination
 a) an elongated stick,
 b) pH indicating first means on the stick, at one end portion thereof,
 c) color comparison pH measurement second means on the stick, spaced from that one end portion thereof,
 d) the stick projecting freely from the first and second means for manual manipulation to first obtain pH indication of vaginal moisture at one end of the stick, and to enable visual interpretation of that indication by color Comparison with the second means, without manual release of the stick,
 e) the stick then being disposable to dispose of both first and second means in one disposal step.

The first means typically comprises a strip adhered to one end of the stick, with the second means then extending lengthwise along the stick, away from the first means; and the second means typically has color gradations in a series sequence lengthwise along the stick.

An additional object includes the provision in the referred apparatus of a swabbing means attached to the stick at the opposite end thereof, and in spaced relation to first and second means. In this regard, the swabbing means and second means typically have stick spacing therebetween of between 3 and 5 inches, enabling ready finger grasping of the stick and manipulation thereof, including rapid endwise reversal of the stick.

These and other objects and advantages of the invention, as well as the details of an illustrative embodiment, will be more fully understood from the following specification and drawings, in which:

DRAWING DESCRIPTION

DETAILED DESCRIPTION

Figure 1:
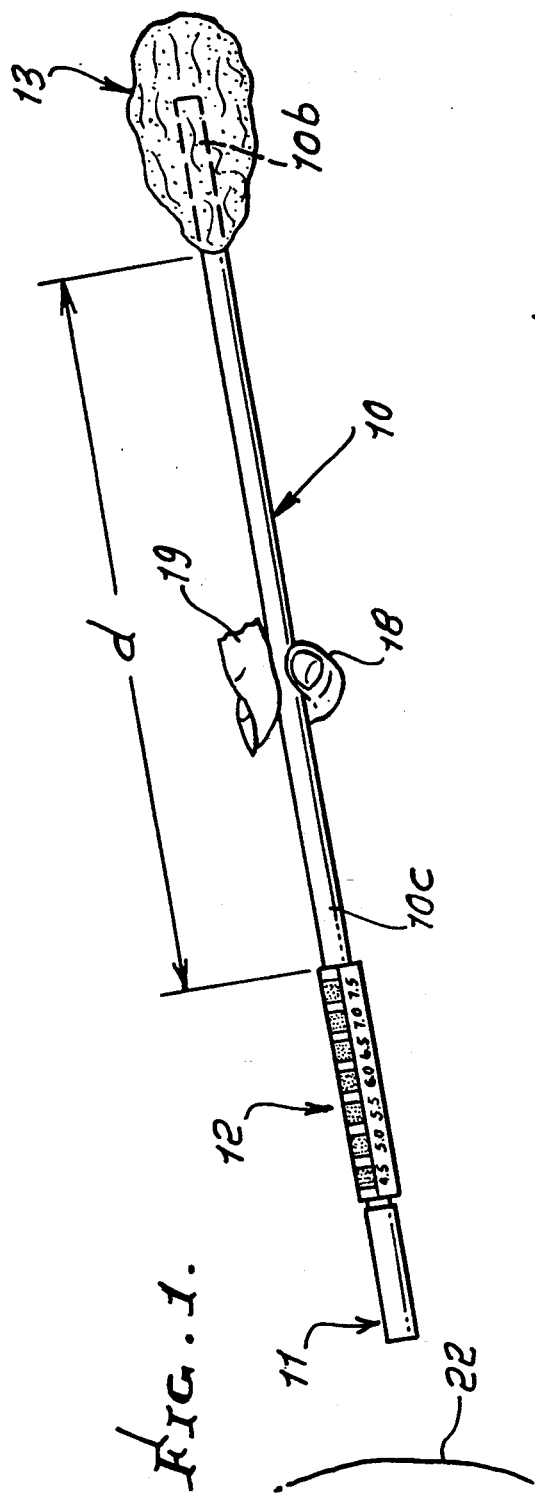
FIG. 1 is a side elevational view of stick apparatus incorporating the invention.
Figure 2:
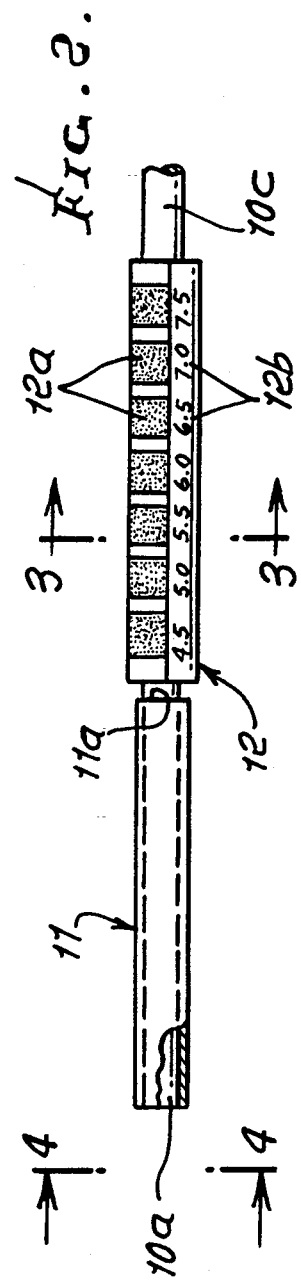
FIG. 2 is an enlarged side view of one end portion of the FIG. 1 stick apparatus.
Figure 3:
FIG. 3 is an enlarged section taken on lines 3—3 of FIG. 2.
Figure 4:
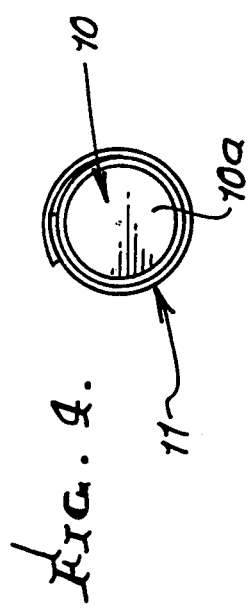
FIG. 4 is an enlarged end view taken on lines 4—4 of FIG. 2.

In the drawings, an elongated, narrow carrier stick 10 may consist of wood, plastic, or other material. Provided on the carrier stick are:
 a pH indication means, as generally shown at 11, at one end portion 10a of the stick;
 a color comparison pH measurement means, as generally indicated at 12, spaced from stick end portion 10a, but close to 11; and
 a swabbing means, as generally indicated at 13 on the opposite end portion 10b of the stick.

As shown, the first means 11 may comprise a pH indication strip, such as a Nytrazine strip, wound about the stick end portion 10a and adhered to same as by an adhesive. A Nitrazine strip is a phenaphthazine paper strip. Nitrazine paper is a known phenaphthazine paper product distributed by E. R. Squibb & Sons, Princeton, N.J. The color comparison pH measurement means 12 may comprise a thin paper strip adhered to the stick surface to extend lengthwise of the stick from the edge or end 11a of the first means 11. The second means is shown to have color gradations in a series sequence, as in colored bands 12a, positioned lengthwise of or along the stick. In addition, the paper strip 12 may include pH numerical indicators 12b along side the color gradation bands, to enable:

visual color comparison of the pH indication means 11 (immediately after its exposure to vaginal fluid) with the bands 12a, for visual selection of that band most close in color to the color of the indication means 11;

and immediate visual readout of the pH number adjacent the selected band.

The stick projects freely at 10c away from the first and second means 11 and 12 for manual manipulation (see the grasping finger and thumb 18 and 19), to first obtain pH indication of vaginal moisture at one end of the stick, and to enable visual interpretation of that indication by color comparison with the second means, without manual release of the stick. The stick is then disposable, or may be disposed of, after a swabbing step to be described.

The swabbing means 13 may comprise a soft cotton swab, or other absorbent material, attached to the carrier stick at its opposite end, and in spaced relation to the first and second means 11 and 12. The lengthwise spacing "d" between 13 and 12 is such as to enable free manual manipulation of the stick; and such spacing is typically between 3 and 5 inches, enabling ready finger grasping of the stick and manipulation thereof, including rapid endwise reversal of the stick. In a specific example, "d" is about 4 inches, and the stick diameter is about ⅜ inch.

The method of measuring pH of vaginal moisture includes the steps:

a) providing a pH indication, color comparison measurement, and swabbing means on a carrier stick, b) manipulating the stick between its opposite ends to obtain pH indication of vaginal moisture at one end of the stick, c) visually interpreting that indication to also obtain pH measurement of such moisture near that one end of the stick, d) again manipulating the stick between its opposite ends, including endwise reversing it, to swab the vaginal cavity in the area from which pH indication was obtained, e) and disposing of the stick, whereby disposition of the pH indication, measurement and swabbing means is thereby obtained in one disposal step.

The overall sizes of 11, 12 and 13 are such as to enable ready insertion into the vagina, via stick manipulation at zone 10c, with ready stick reversal, as needed. Swabbing of the vagina 22 is typically carried out in conjunction with pH measurement, via stick manipulation and endwise reversal, to obtain best measurement results.

I claim:

1. In the method of measuring pH of vaginal moisture, the steps that include:

a) providing a pH indication, color comparison measurement, and swabbing means on a carrier stick, b) manipulating the stick between its opposite ends to obtain pH indication of vaginal moisture at one end of the stick, c) visually interpreting that indication to also obtain pH measurement of such moisture near that one end of the stick, d) again manipulating the stick between its opposite ends, including endwise reversing it, to swab the vaginal cavity in the area from which pH indication was obtained, e) and disposing of the stick, whereby disposition of the pH indication, measurement and swabbing means is thereby obtained in one disposal step, f) said step a) including adhering an elongated pH indication strip to said one end of the stick and adhering an elongated pH measurement colorimeter strip to the stick adjacent said pH indication strip and in direct alignment with said indication strip and said swabbing means, each strip adhered to the stick to extend about the stick.

2. The method of claim 1 wherein said colorimeter strip is adhered to the stick adjacent an end of said pH indication strip and between said indication strip and said swabbing means.

3. The method of claim 2 including maintaining a gap along the stick length between said pH measurement means and said swabbing means, whereby the stick may be readily grasped at said gap for said manipulation.

4. The method of claim 3 wherein said gap is maintained to have a length between 3 and 5 inches.

5. The method of claim 3 wherein said gap is provided to have a length of about 4 inches.

6. The method of claim 1 wherein said pH measurement means is provided to have color gradations in a series sequence, and including locating said series lengthwise along the stick, and to extend about the stick.

7. The method of claim 6 including maintaining a gap along the stick length between said pH measurement means and said swabbing means, whereby the stick may be readily grasped at said gap for said manipulation without manual interference with any of said a) means.

8. The method of claim 6 wherein said pH measurement means also provided to have a pH numerical sequence in a series associated with said color gradations, and including also locating said numerical sequence lengthwise along the stick.

9. The method of claim 1 wherein said pH indication strip is provided by winding it about said one end of the stick, and adhering it thereto.

10. The method of claim 1 wherein said swabbing means is provided by attaching a moisture-absorbing swab to the other end of said stick, and in spaced relation to both said pH indicating means and said pH measurement means.

11. The method of claim 1 wherein swabbing is effected both prior to and subsequent to the obtaining of pH indication, by endwise stick reversal, to facilitate rapid pH measurement.

12. In apparatus for measuring pH of vaginal moisture, the combination comprising:

a) an elongated carrier stick, b) pH indicating first means on the stick, at one end portion thereof, c) color comparison pH measurement second means on the stick, spaced from said one end portion thereof, d) the stick projecting freely from said first and second means for manual manipulation to first obtain pH indication of vaginal moisture at said one end of the stick, and to enable visual interpretation of that indication by color comparison with said second means, without manual release of the stick, e) the stick then being disposable to dispose of both said first and second means in one disposal step, f) said first means comprising a first strip adhered to said one end of the stick, and said second means comprising a second strip that extends lengthwise along the stick, away from one end of said first strip, each strip extending annularly about the stick, said strips being in direct endwise alignment.

13. The apparatus of claim 12 wherein said second strip is adhered to the stick to extend lengthwise along the stick, away from said one end of said first strip and in linear alignment therewith.

14. The apparatus of claim 13 wherein said second strip has color gradations in a series sequence lengthwise along the stick, said gradations extending at least part way about the stick.

15. The apparatus of claim 14 wherein there are pH numerical indications on the stick, in close association with said color gradations.

16. The apparatus of claim 13 wherein said first means comprises a strip.

17. The apparatus of claim 16 wherein said strip is wound about the stick, or by other means attached, at said one end thereof.

18. The apparatus of claim 12 including a vaginal moisture swabbing means attached to the stick at the opposite end thereof, and in spaced relation to said first and second means.

19. The apparatus of claim 18 wherein the swabbing means and second means have stick spacing therebetween of between 3 and 5 inches, enabling ready finger grasping of the stick and manipulation thereof, including rapid endwise reversal of the stick.

20. The apparatus of claim 19 wherein said spacing is about 4 inches.

* * * * *